United States Patent
Zarrinpar

(10) Patent No.: US 12,044,683 B2
(45) Date of Patent: Jul. 23, 2024

(54) METHODS AND COMPOSITIONS CONCERNING INTESTINAL PERMEABILITY

(71) Applicants: THE REGENTS OF THE UNIVERSITY OF CALIFORNIA, Oakland, CA (US); UNIVERSITY OF FLORIDA RESEARCH FOUNDATION, Gainesville, FL (US)

(72) Inventor: Ali Zarrinpar, Oakland, CA (US)

(73) Assignee: University of Florida Research Foundation, Inc., Gainesville, FL (US)

(*) Notice: Subject to any disclaimer, the term of this patent is extended or adjusted under 35 U.S.C. 154(b) by 1031 days.

(21) Appl. No.: 16/964,437

(22) PCT Filed: Jan. 25, 2019

(86) PCT No.: PCT/US2019/015227
§ 371 (c)(1),
(2) Date: Jul. 23, 2020

(87) PCT Pub. No.: WO2019/147990
PCT Pub. Date: Aug. 1, 2019

(65) Prior Publication Data
US 2021/0048438 A1 Feb. 18, 2021

Related U.S. Application Data

(60) Provisional application No. 62/623,033, filed on Jan. 29, 2018, provisional application No. 62/622,669, filed on Jan. 26, 2018.

(51) Int. Cl.
| | | |
|---|---|---|
| *G01N 33/58* | (2006.01) | |
| *A23L 5/47* | (2016.01) | |
| *G01N 21/31* | (2006.01) | |
| *G01N 30/72* | (2006.01) | |
| *G01N 30/02* | (2006.01) | |

(52) U.S. Cl.
CPC ............... *G01N 33/58* (2013.01); *A23L 5/47* (2016.08); *G01N 21/31* (2013.01); *G01N 30/7233* (2013.01); *A23V 2002/00* (2013.01); *G01N 2030/027* (2013.01); *G01N 2800/06* (2013.01); *G01N 2800/56* (2013.01)

(58) Field of Classification Search
CPC ......... A23L 5/47; A23L 5/40; A23V 2002/00; G01N 2030/027; G01N 21/31; G01N 2800/06; G01N 2800/56; G01N 30/7233; G01N 33/58; A61P 1/00
See application file for complete search history.

(56) References Cited

U.S. PATENT DOCUMENTS

| | | | | |
|---|---|---|---|---|
| 2004/0229842 | A1* | 11/2004 | Yedgar | A61P 37/02 514/56 |
| 2014/0147856 | A1 | 5/2014 | Forsyth et al. | |

OTHER PUBLICATIONS

Krimsky et al., "Assessment of intestinal permeability in rats by permeation of inulin-fluorescein," Basic Clin. Physiol. Pharmacol., 2000, vol. 11, No. 2, pp. 143-153.*
Carpenito et al., "Green urine in a critically ill patient," Am. J. Kidney Dis., 2002, vol. 39, issue 4, pp. e20.1-e20.5.*
International Search Report issued for PCT/US2019/015227, mailed Mar. 22, 2019.
Rera et al., Intestinal barrier dysfunction links metabolic and inflammatory markers of aging to death in Drosophila, PNAS, vol. 109, No. 52, p. 21528-21533, 2012.
Rera et al., Modulation of Longevity and Tissue Homeostasis by the Drosophila PGC-1 Homolog, Cell Metabolism, vol. 14, p. 623-634, 2011.
Angarita et al., Quantitative Measure of Intestinal Permeability Using Blue Food Coloring, Journal of Surgical Research, vol. 233, pp. 20-25, 2018.
Dellinger, R. Phillip, et al., "Surviving Sepsis Campaign: International Guidelines for Management of Severe Sepsis and Septic Shock: 2012," CCM Journal, vol. 41, No. 2 (2013), pp. 580-637.
Berge, Stephen M., et al., "Pharmaceutical Salts, Journal of Pharmaceutical Sciences," vol. 66, No. 1 (1977), (19 pages).

* cited by examiner

*Primary Examiner* — Galina M. Yakovleva
(74) *Attorney, Agent, or Firm* — Thomas|Horstemeyer, LLP

(57) ABSTRACT

Methods, assays and compositions for measuring intestinal permeability in subjects are provided. The methods and assays comprise the measurement of the level of food dyes, such as FD&C Blue No. 1, in blood samples shortly after the ingestion of the compositions. The methods disclosed herein are simple, cost-effective, reproducible and sensitive.

14 Claims, 12 Drawing Sheets

| Standard Curves Experiment 12.27.2016 | | | | | | | | |
|---|---|---|---|---|---|---|---|---|
| fMoles injected | | | | Average | sem | | | |
| 100000 | 262551 | 261959 | 254325 | 259611.7 | 2648.9 | | | |
| 50000 | 146727 | 142590 | 137429 | 136446.7 | 2689.5 | 138919 | 136360 | 134061 |
| 20000 | 48259 | 47064 | 44881 | 46741.3 | 980.1 | | | |
| 10000 | 18817 | 17848 | 17828 | 18164.3 | 326.4 | | | |
| 5000 | 7956 | 7695 | 7216 | 7622.3 | 216.7 | | | |
| 2000 | 2822 | 2652 | 2517 | 2663.7 | 88.2 | | | |
| 1000 | 1369 | 1257 | 1159 | 1261.7 | 60.7 | | | |
| 500 | 521 | 468 | 436 | 521.0 | 24.8 | | | |
| 200 | 200 | 187 | 186 | 191.0 | 4.5 | | | |
| 100 | 107 | 93 | 99 | 99.7 | 4.1 | | | |
| 50 | 51 | 45 | 53 | 49.7 | 2.4 | | | |
| 20 | 16 | 21 | 23 | 20.0 | 2.1 | | | |
| 10 | | | | | | | | |
| 5 | | | | | | | | |
| 2 | | | | | | | | |
| 1 | | | | | | | | |

FIG. 5A

| fMoles injected | Standard Curves Experiment 9.7.2016 | | Average |
|---|---|---|---|
| 50000 | 38896 | | 38896 |
| 30000 | | | |
| 20000 | 6510 | | 6510 |
| 10000 | 2807 | | 2807 |
| 5000 | 1311 | | 1311 |
| 2000 | 885 | 424 | 566.6666667 |
| 1000 | 311 | 391 | 311 |
| 500 | 74 | | 74 |
| 200 | 61 | | 61 |
| 100 | 31 | | 31 |
| 50 | | | |
| 20 | | | |
| 10 | | | |
| 5 | | | |
| 2 | | | |
| 1 | | | |

FIG. 6A

Standard Curves
Experiment 2.26.2016

| fMales Injected | | | | Average | sem |
|---|---|---|---|---|---|
| 50000 | | | | | |
| 30000 | 70687 | 67844 | | 69265.5 | 1160.6 |
| 20000 | 43381 | 45338 | | 44359.5 | 798.9 |
| 10000 | 21239 | 21545 | 21643 | 21475.7 | 121.7 |
| 5000 | 9286 | 9551 | 9406 | 9414.3 | 76.6 |
| 2000 | 3575 | 3688 | 3614 | 3625.7 | 33.1 |
| 1000 | 1908 | 1903 | 1894 | 1901.7 | 4.1 |
| 500 | 889 | 849 | 860 | 866.0 | 11.9 |
| 200 | 455 | 454 | 454 | 454.3 | 0.3 |
| 100 | 308 | 314 | 322 | 314.7 | 4.1 |
| 50 | | | | | |
| 20 | | | | | |
| 10 | | | | | |
| 5 | | | | | |
| 2 | | | | | |
| 1 | | | | | |

FIG. 7A

The higher dome (in dark violet) is with 2000 fmoles at ESI
The lower dome (in red) is with 2000 fmoles at ESI

METHODS AND COMPOSITIONS CONCERNING INTESTINAL PERMEABILITY

CROSS-REFERENCE TO RELATED APPLICATIONS

This application is a National Stage of International Application No. PCT/US2018/015227, filed Jan. 25, 2019, which claims benefit of U.S. Provisional Application No. 62/622,669, filed Jan. 26, 2018, and Application Ser. No. 62/623,033, filed Jan. 29, 2018, which are hereby incorporated herein by reference in their entirety.

BACKGROUND

There is mounting evidence that intestinal barrier integrity loss plays a key role in the development and perpetuation of a variety of disease states, such as inflammatory bowel and celiac disease and sepsis. Intestinal barrier loss also plays a major role in the onset of sepsis and multiple organ failure in situations of intestinal hypoperfusion, including trauma and major surgery, or in the setting of abnormal blood flow such as portal hypertension. Insight into gut barrier integrity and function loss is important to attempt to improve knowledge on disease etiology and pathophysiology and contributes to early detection and/or secondary prevention of disease.

A variety of tests have been developed to assess intestinal epithelial cell damage, intestinal tight junction status, and the consequences of intestinal barrier integrity loss, i.e. increased intestinal permeability. One method is to assess epithelial barrier integrity by measuring fatty acid binding proteins, glutathione S-transferase, or claudin-3 in the blood or urine. Measuring various sugars or polytheylene glycol have been used as an active measure of intestinal barrier function. These methods, however, suffer from a lack of sensitivity, a prolonged period of collection (for the urinary tests), or high expense.

In view of the importance of the role played by intestinal barrier integrity in the development and perpetuation of a variety of disease states and in view of the limitations of known tests in measuring intestinal permeability, there is a need in the art for a sensitive, cost-effective, reproducible, easy to use, uncomplicated test for intestinal permeability in subjects, particularly in humans for example.

SUMMARY

The present disclosure relates to methods and compositions involving food dyes for testing intestinal permeability. Embodiments of the present disclosure provides a technique to measure the concentration of a nonabsorbable, non-digestable compound, such as a nonabsorbable, non-digestable dye, in a blood sample from the patient and a method of applying this technique in measuring intestinal barrier function or intestinal permeability in humans. In some embodiments, the nonabsorbable, non-digestible dye is Brilliant Blue FCF (disodium;2-[[4-[ethyl-[(3-sulfonatophenyl)methyl]amino]phenyl]-[4-[ethyl-[(3-sulfonatophenyl)methyl]azaniumlidene]cyclohexa-2,5-dien-1-ylidene]methyl]benzenesulfonate) (referred to herein as "Blue #1").

Embodiments include inter glia methods of assaying for or measuring the concentration of nonabsorbable, non-digestable compound in a blood sample from a subject; methods for measuring a component in the blood sample of a patient; methods of assessing intestinal barrier integrity in a subject; methods for evaluating intestinal permeability; methods of determining increased intestinal permeability in a subject; methods of assessing disease state in a subject, methods of reducing risk of disease associated with increased intestinal permeability in a subject; methods of diagnosing a patient with loss of intestinal integrity; method for treating a patient; methods of using a nonabsorbable, non-digestable compound/dye to assess intestinal integrity; and/or methods of using a nonabsorbable, non-digestable compound/dye to determine increased intestinal permeability in a subject. The steps and embodiments discussed in this disclosure are contemplated as part of any of these methods. Moreover, compositions for use in any of these methods are also contemplated. For example, embodiments include assays for measuring a nonabsorbable, non-digestable compound/dye in a blood sample, as well as compositions and kits comprising a nonabsorbable, non-digestable compound/dye for use in assays. Subjects or patients may be mammals, particularly humans, monkeys, chimpanzees, gorillas, rabbits, horses, cows, sheep, pigs, goats, dogs, or cats. Other animals may be included such as chickens, avians, fish, reptiles, or other animals with an intestinal barrier. In particular embodiments, the animal is a warm- or cold-blooded animal.

Methods may comprise, consist of, or consist essentially of the following steps: administering to the patient a pharmaceutical composition comprising a nonabsorbable, non-digestable compound; obtaining a blood sample from the subject; assaying the blood sample to measure or quantify the nonabsorbable, non-digestable compound; comparing the amount of nonabsorbable, non-digestable compound in the blood sample to a control; evaluating the subject's intestinal barrier integrity; diagnosing and/or prognosing the subject based on the integrity of the subject's intestinal barrier; and/or treating the subject based on an evaluation of the integrity of the subject's intestinal. One or more of these steps may be included or excluded in methods.

Therefore, disclosed are methods that involve assaying a blood sample from a subject for nonabsorbable, non-digestable compound after the subject has been administered a pharmaceutical composition comprising nonabsorbable, non-digestable compound.

In some embodiments, the disclosed method involves administering to the subject's a pharmaceutical composition comprising Blue #1; assaying or measuring Blue #1 in a blood sample collected from the patient within 24 hours after the patient has been administered the oral pharmaceutical composition; and evaluating the integrity of the patients intestinal barrier based on the amount of Blue #1 measured in the blood sample.

In certain embodiments, the pharmaceutical composition is/was a liquid composition. In other embodiments, the composition is a paste, gel, film, tablet, pill, capsule, spray or solid formulation. In some embodiments, the volume of the pharmaceutical composition is/was about, at least about, or at most about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 µl or ml (or any range derivable therein). In certain embodiments, the volume of the pharmaceutical composition is or was between about 1 ml and about 500 ml. In other embodiments, the volume of the pharmaceutical composition was between about 5 ml and about 100 ml. In additional embodiments the volume of the pharmaceutical composition is or was between about 10 ml and about 50 ml. The concentration of nonabsorbable, non-digestable compound/dye in the pharmaceutical composition may be 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 µM or mM (or any range derivable therein). Alternatively, it may constitute about, at least about, or at most about 50, 55, 60, 65, 70, 75, 80, 85, 90, 95, 96, 97, 98, 99, or 100% (or any range derivable therein) of the active ingredients or components in the pharmaceutical composition.

The amount of a single dose of nonabsorbable, non-digestible compound/dye that is or was administered to a subject in the disclosed methods is about, at least about, or at most about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 65, 70, 75, 80, 85, 90, 95, 100, 105, 110, 115, 120, 125, 130, 135, 140, 145, 150,155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 µg/kg or mg/kg (or any range derivable therein). In some embodiments, the patient was or is administered about 1 mg/kg or less of nonabsorbable, non-digestable compound/dye in a single dose of the pharmaceutical composition. In other embodiments, the patient is administered about 0.5 mg/kg or less in a single dose of the pharmaceutical composition. In other embodiments, the total amount of nonabsorbable, non-digestable compound/dye that is or was administered to the patient is about, at least about, or at most about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 µg/kg or mg/kg (or any range derivable therein). The patient may be or may have been given a single dose or multiple doses of a pharmaceutical composition consisting essentially of a nonabsorbable, non-digestable compound/dye, and the total amount is about, at least about, or at most about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 µg or mg (or any range derivable therein). There may be 1, 2, 3, 4, 5, 6, 7, 8, 9, 10, 11, 12 or more multiple doses that are given. Multiple doses may have been given to the patient over a period of time that is 1, 2, 3, 4, 5, 6, 7, 8, 9, 10, 11, 12, 13, 14, 15, 16, 17, 18, 19, 20, 21, 22, 23, 24 hours, and/or 1 2, 3, 4, 5, 6, 7 days, and/or 1, 2, 3, 4, 5, 6, 7, 8, 9, 10, 11, 12 or more weeks. It is contemplated that there may be gaps of time between the administration of doses. For instance, treatment may be evaluated for days, weeks, or months, before the patient's intestinal permeability is evaluated again. Alternatively, the dye may be given multiple times and after about, at most about, or at least about 10, 20, 30, 40, 50, 60 minutes, and/or 1, 2, 3, 4, 5, 6, 7, 8, 9, 10, 11, 12, 13, 14, 15, 16, 17, 18, 19, 20, 21, 22, 23, or 24 hours (or any range derivable therein) when the previous dose was administered.

In some embodiments, the pharmaceutical composition comprising or consisting essentially of the nonabsorbable, non-digestible compound/dye is/was administered to the patient orally or nasogastrically.

In some embodiments, one or more blood samples from the patient are assayed or evaluated. In some embodiments, 1, 2, 3, 4, 5, 6, 7, 8, 9, 10, 11, or 12 blood samples from the patient (or any range derivable therein) are assayed or evaluated. Some methods include a step of collecting, extracting, or drawing a blood sample directly from the patient. In additional embodiments, the volume of the blood sample is about, at least about, or most about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 65, 70, 75, 80, 85, 90, 95, 100 µl or ml orc (or any range derivable therein). The blood sample may be from a drop of blood or it may be a draw of a larger quantity of blood.

In some embodiments, the blood sample is a plasma or serum sample. Plasma may be subjected to one or more chemicals that lyse, precipitate, and/or extract components. It may then be physically manipulated such as through centrifugation, evaporation, and/or resuspension. In some embodiments, liquid extraction or solid phase extraction is employed on the sample.

In some embodiments, the blood sample may be evaluated at about, within about, or after about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60, minutes, and/or 1, 2, 3, 4, 5, 6, 7, 8, 9, 10, 11, 12, 13, 14, 15, 16, 17, 18, 19, 20, 21, 22, 23, 24 hours (or any range derivable therein) from when the patient was most recently administered a pharmaceutical composition comprising or consisting essentially of a nonabsorbable, non-digestable compound/dye. In certain embodiments, assaying is done from a sample collected from the patient up to 2, 4, or 8 hours after the patient has been administered a pharmaceutical composition comprising a nonabsorbable, non-digestable compound/dye.

Assaying, measuring, evaluating, and/or quantifying the nonabsorbable, non-digestible dye in a biological sample such as blood may be done using mass spectrometry and/or high performance liquid chromatography (HPLC) and/or light spectroscopy. In some embodiments, the nonabsorbable, non-digestable dye is attached to a detectable molecule, such as a radioactive molecule, and the dye is detected by detecting the label.

In some embodiments, the subject has been diagnosed with, has symptoms of, or is at risk for ascites, sepsis, intestinal hypoperfusion, celiac disease, Crohn's disease, type 2 diabetes, rheumatoid arthritis, inflammatory bowel disease, spondyloarthropathies, irritable bowel syndrome, schizophrenia, cancer, obesity, fatty liver, atopy, an allergic disease, bowel injury, bowel perforation, graft-versus-host-disease, typhlitis, or post-chemotherapy bowel inflammation.

In some embodiments, the subject has experienced trauma or major surgery within 6, 12, 18, 24, 30, 36, 42, 48, 54, 60, 66, or 72 hours (or any range derivable therein) prior to being administered the pharmaceutical composition. In some embodiments, the subject has been diagnosed with sepsis, intestinal hypoperfusion, celiac disease, trauma, organ failure, or inflammatory bowel disease.

In some cases, the subject has not ingested any liquid or food within 1, 2, 3, 4, 5, 6, 7, 8, 9, 10, 11, 12, 13, 14, 15, 16, 17, 18, 19, 20, 21, 22, 23, or 24 hours (or any range derivable therein) prior to being administered the pharmaceutical composition comprising the nonabsorbable, non-digestable compound/dye.

In certain embodiments, the method involves comparing the amount of nonabsorbable, non-digestible compound/dye in a blood sample from a patient to a control amount or a control sample. The control amount or sample may be negative or positive with respect to presence or absence of the nonabsorbable, non-digestible compound/dye.

In certain embodiments, the pharmaceutical composition comprising the nonabsorbable, non-digestible compound/dye also comprises a positive control that permeates the intestinal barrier. The positive control should be dectable in blood (or urine) without modification. An example of a positive control is Blue #2 (i.e. indigo carmine, 3,3'-dioxo-2,2'-bisindolyden-5,5'-disulfonic acid disodium salt).

In some embodiments, the amount of nonabsorbable, non-digestible compound/dye detected, measured, or quantified is about, at least about, or at most about $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$ M or any range derivable therein.

In some embodiments, the blood sample from the patient has no detectable amounts of nonabsorbable, non-digestable compound/dye. A patient may be determined not to have intestinal permeability. In other embodiments, the patient may be determined to have intestinal permeability, which may be indicative of a disease or condition. In some embodiments, the patient having intestinal permeability nonabsorbable, non-digestable compound/dye measured to be at least 1 femtomole per 5 ml of the patient's blood sample.

In additional embodiments, the subject may be treated for the disease or condition. For example, in some cases the nonabsorbable, non-digestable compound/dye is measured to be at least about 1 femtomole per 5 ml in the blood sample, and the method further comprises treating the subject for intestinal barrier dysfunction. Examples of treatments include stopping enteric feeding, administration of intestinal antibiotics, administration of probiotics, administration of intravascular antibiotics, or any combination thereof.

Also disclosed herein is a pharmaceutical composition comprising about 0.1 mg to 1500 mg Blue #1 and a pharmaceutically acceptable excipient for oral administration. In some embodiments, the pharmaceutical composition comprises about 0.1 to 50 mg Blue #1, about 0.1 to 100 mg Blue #1, about 0.1 to 500 mg Blue #1, about 0.1 to 1000 mg Blue #1, about 0.1 to 1500 mg Blue #1, about 0.5 mg to 50 mg Blue #1, about 0.5 to 100 mg Blue #1, about 0.5 to 500 mg Blue #1, about 0.5 to 1000 mg Blue #1, or about 0.5 to 1500 mg Blue #1.

Also disclosed is a kit comprising the herein disclosed pharmaceutical composition and a plurality of standards comprising Blue #1 in known amounts for producing a standard curve.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

The details of one or more embodiments of the invention are set forth in the accompanying drawings and the description below. Other features, objects, and advantages of the invention will be apparent from the description and drawings, and from the claims.

DETAILED DESCRIPTION

Definitions

Figure 1:
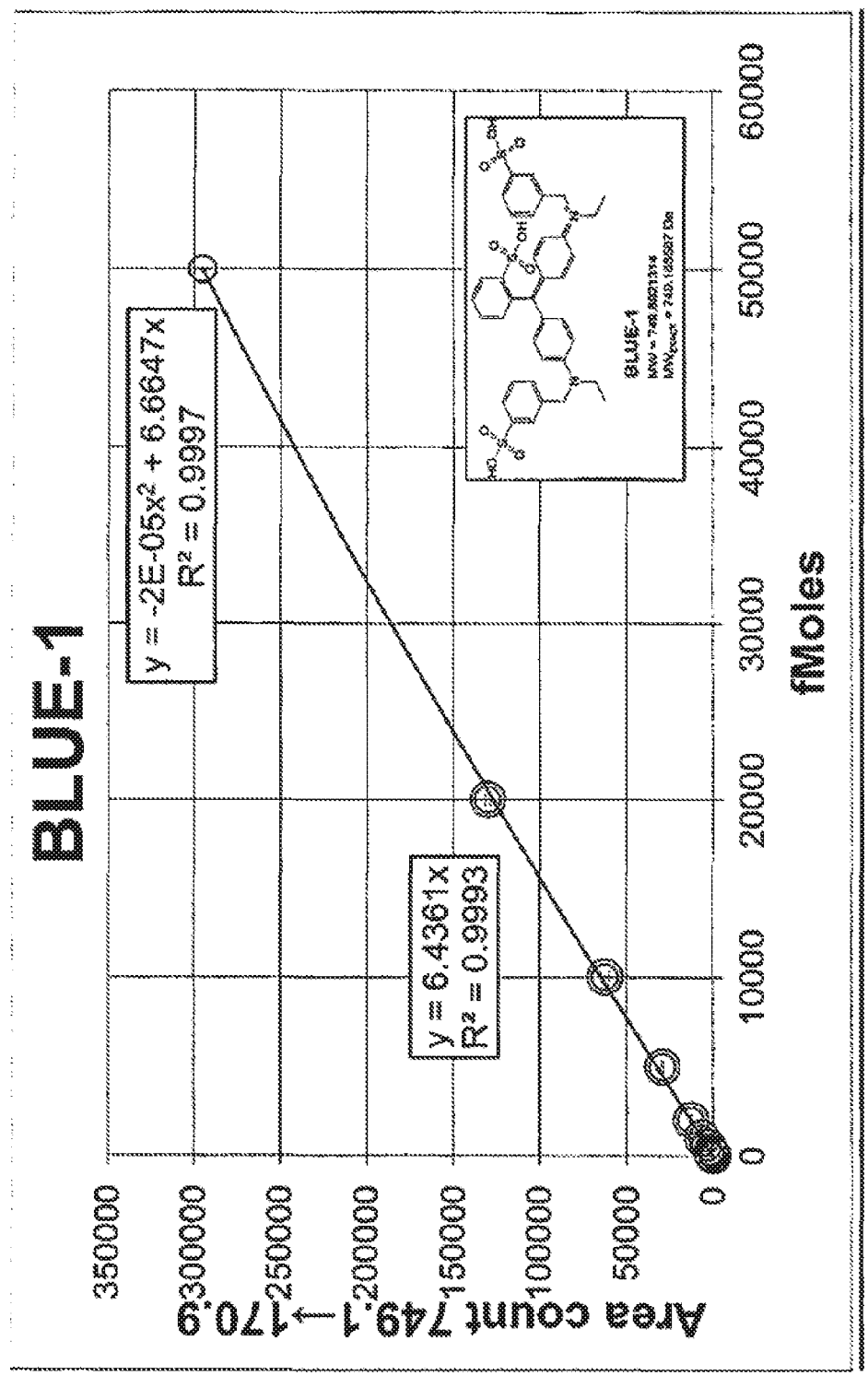
FIG. 1 depicts a graph highlighting the sensitivity of an assay/test in accordance with the current invention. Amounts as small as 1 femtomole ($10^{15}$) can be detected.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"Diagnosis" may refer to the process of attempting to determine or identify a possible disease or disorder, or to the opinion reached by this process, From the point of view of statistics the diagnostic procedure may involve classification tests.

"Prognosis" may refer to a prediction of how a patient will progress, and whether there is a chance of recovery. Prognosis may also include prediction of favorable responses to treatments, such as a conventional therapy.

By "subject" or "patient" is meant any single subject for which therapy is desired, including humans, cattle, dogs, guinea pigs, rabbits, chickens, and so on. Also intended to be included as a subject are any subjects involved in clinical research trials not showing any clinical sign of disease.

As used herein, the term "biological fluid" refers to a fluid containing cells and compounds of biological origin, and may include blood, stool or feces, lymph, urine, serum, pus, saliva, seminal fluid, tears, urine, bladder washings, colon washings, sputum or fluids from the respiratory, alimentary, circulatory, or other body systems.

There is a need for a reliable, easy to use, and sensitive test to evaluate diseases affecting the intestinal barrier of a patient. Embodiments concerns methods and compositions involving nonabsorbable food dyes.

Some dyes appear not to be absorbed by fruit flies, such as FD&C Blue #1, based on viewing fruit fly bodies under a microscope after they were given the dye (Rera, Clark and Walker. PNAS 2012). In these studies, Blue #1 was used to test intestinal integrity, Loss of this integrity was found to be associated with altered metabolic and immune signally and, critically was shown to be a harbinger of death. While FD&C Blue #1 is a water-soluble dye that has been approved by the FDA for use in foods, drugs, and cosmetics with studies supporting an acceptable daily intake of 12 mg/kg body weight/day, there have been reports of adverse events, including deaths, associated with the use of blue dye in tube feedings especially in patients with a reported history of sepsis. This emphasizes the importance of measuring the changes in the intestinal absorption of Blue #1 in a variety of clinical settings, not just in normal subjects. In the Examples shown below, such measurements were done and they showed that a blood sample from a patient could be used to assess intestinal barrier integrity using a nonabsorbable dye.

Alternatively, the sample may include but not be limited to blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample.

In some embodiments, methods will involve determining or calculating a diagnostic or risk score based on data concerning the amount of Blue #1 in the blood sample of the patient. A diagnostic score will provide information about the biological sample, such as the general probability that the patient is at high or significant risk for developing one of the diseases disclosed herein, or is at low risk for developing a disease or condition related to the permeability of the patient's intestine.

The skilled artisan will recognize, however, that there are many different methods for evaluating the presence or absence of Blue #1, e.g., thin layer chromatography (TLC), high performance liquid chromatography (H PLC), mass spectrometry (MS), nanopore amperometry, microarrays, and matrix-assisted laser desorption ionization time-of-flight (MALDI-TOF) mass spectrometry.

Suitable preparations, e.g., substantially pure preparations of the agents described herein may be combined with pharmaceutically acceptable carriers, diluents, solvents, excipients, etc., to produce an appropriate pharmaceutical composition. The embodiment therefore provides a variety of pharmaceutically acceptable compositions for administration to a subject comprising (i) an antibiotic potentiating agent; and (ii) a pharmaceutically acceptable carrier or excipient. The embodiment further provides a pharmaceutically acceptable composition comprising (i) an antibiotic potentiating agent; (ii) an antibiotic whose activity is potentiated by the compound; and (iii) a pharmaceutically acceptable carrier or excipient. The embodiment further provides a pharmaceutically acceptable unit dosage form containing a predetermined amount of an antibiotic and a predetermined amount of an antibiotic potentiating agent, wherein the predetermined amounts are selected so that the antibiotic potentiating agent potentiates the antibiotic when the unit dosage form is administered to a subject.

Further provided are pharmaceutically acceptable compositions comprising a pharmaceutically acceptable derivative (e.g., a prodrug) of any of the potentiating agents of the embodiments, by which is meant any non-toxic salt, ester, salt of an ester or other derivative of a potentiating agent, upon administration to a recipient, is capable of providing, either directly or indirectly, the potentiating agent. A wide variety of appropriate pharmaceutically acceptable salts are well known in the art. For example, S. M. Berge et al., describe pharmaceutically acceptable salts in detail in J. Pharmaceutical Sciences, 66:1, 1977, incorporated herein by reference. Pharmaceutically acceptable salts of the compounds of this embodiment include those derived from suitable inorganic and organic acids and bases.

The term "pharmaceutically acceptable carrier, excipient, or vehicle" refers to a non-toxic carrier, excipient, or vehicle that does not destroy the pharmacological activity of the agent with which it is formulated. Pharmaceutically acceptable carriers, excipients, or vehicles that may be used in the compositions of this embodiment include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of a compound, can also be incorporated into the compositions.

Pharmaceutically acceptable salts of the agents of this embodiment include those derived from pharmaceutically acceptable inorganic and organic acids and bases, Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the embodiment and their pharmaceutically acceptable acid addition salts.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2 ethanedisulfonic acid, 2 hydroxyethanesulfonic acid, 2 naphthalenesulfonic acid, 3 phenylpropionic acid, 4,4' methylenebis(3 hydroxy 2 ene-1 carboxylic acid), 4 methylbicyclo[2.2.2]oct 2 ene-1 carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, mucomc acid, o (4 hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., Verlag Helvetica Chimica Acta, 2002).

Suitable preparations, e.g., substantially pure preparations of the agents described herein may be combined with pharmaceutically acceptable carriers, diluents, solvents, excipients, etc., to produce an appropriate pharmaceutical composition. The embodiment therefore provides a variety of pharmaceutically acceptable compositions for administration to a subject comprising (i) an antibiotic potentiating agent; and (ii) a pharmaceutically acceptable carrier or excipient. The embodiment further provides a pharmaceutically acceptable composition comprising (i) an antibiotic potentiating agent; (ii) an antibiotic whose activity is potentiated by the compound; and (iii) a pharmaceutically acceptable carrier or excipient. The embodiment further provides a pharmaceutically acceptable unit dosage form containing a predetermined amount of an antibiotic and a predetermined amount of an antibiotic potentiating agent, wherein the predetermined amounts are selected so that the antibiotic potentiating agent potentiates the antibiotic when the unit dosage form is administered to a subject.

A pharmaceutical formulation may comprise a pharmaceutically acceptable derivative (e.g., a prodrug) of a dye in an embodiment, by which is meant any non-toxic salt, ester, salt of an ester or other derivative of a dye, upon administration to a recipient, is capable of providing, either directly or indirectly, the generally impermeable dye or a positive control dye. A wide variety of appropriate pharmaceutically acceptable salts are well known in the art. For example, S. M. Berge et al., describe pharmaceutically acceptable salts in detail in J. Pharmaceutical Sciences, 66:1, 1977, incorporated herein by reference. Pharmaceutically acceptable salts of the compounds of this embodiment include those derived from suitable inorganic and organic acids and bases.

The term "pharmaceutically acceptable carrier, excipient, or vehicle" refers to a non-toxic carrier, excipient, or vehicle that does not destroy the pharmacological activity of the agent with which it is formulated. Pharmaceutically acceptable carriers, excipients, or vehicles that may be used in the compositions of this embodiment include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, di sodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of a compound, can also be incorporated into the compositions.

Pharmaceutically acceptable salts of the agents of this embodiment include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the embodiment and their pharmaceutically acceptable acid addition salts.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2 ethanedisulfonic acid, 2 hydroxyethanesulfonic acid, 2 naphthalenesulfonic acid, 3 phenylpropionic acid, 4,4' methylenebis(3 hydroxy 2 ene-1 carboxylic acid), 4 methylbicyclo[2.2.2]oct 2 ene-1 carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o (4 hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (RH. Stahl & C. G. Wermuth eds., Verlag Helvetica Chimica Acta, 2002).

Pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol or sodium chloride in the composition. Prolonged absorption of injectable compositions can be brought about by including in the composition an agent which delays absorption, for example, aluminum monostearate and gelatin. Prolonged absorption of oral compositions can be achieved by various means including encapsulation.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral administration, the active compound can be incorporated with excipients and used in the form of tablets, films, solutions, gels, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch: a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions are preferably delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The present embodiment also contemplates delivery of compositions using a nasal spray or solution.

A number of embodiments of the invention have been described. Nevertheless, it will be understood that various modifications may be made without departing from the spirit and scope of the invention. Accordingly, other embodiments are within the scope of the following claims.

EXAMPLES

The inventor has developed a technique to measure the concentration of food dyes from blood and a method of applying this technique for measuring intestinal barrier function in humans. Amounts as small as 1 femtomole ($10^{-15}$) can be measured. (FIG. 1). Studies in rats have shown that slightly more than 0.02% of the dye gets absorbed into the blood from the intestine (Brown 1980). Assuming that this then distributes uniformly throughout the body, based on Brown's study, a 70 kg subject drinking 35 ml of Gatorade Blueberry Pomegranate would have more than 500 femtomoles per 5 ml of blood.

Example 1: Establishing Lower Limit of Detection in Normal Subjects and Measuring the Baseline/Normal Intestinal Absorption in Normal Subjects To test the limit of detection of the liquid chromatography/mass spectrometry (LC/MS) based system, the limits of detection were first tested. A higher dose of Blue Dye #1 was first used to increase chances of detecting the dye in the blood and then lower amounts of Blue Dye (to minimize the exposure) were also tested. The highest test load used was still a 24-fold lower amount than the FDA approved safe level. Thus, the use of this safe dye that is approved for oral administration is the safest, cheapest, and most feasible means to measure intestinal permeability.

High dose: 0.5 mg/kg—e.g, 35 mg in a 70 kg adult, administered as 35 ml of diluted food coloring solution (16 mg/mL diluted 1:16) was used. Five blood samples were drawn per subject (5 ml/draw): 0 hour-prior to dose, 1 hour, 2 hours, 4 hours, 8 hours. Four subjects enrolled. There wasn't any detectable absorption in normal subjects even at the high dose of 0.5 mg/kg up to 8 hours later, Next the differences between normal subjects and those with ascites or sepsis were tested.

Example 2

A. Testing in Patients with Ascites

Test subjects were given enteral Blue #1 at a designated time prior to paracentesis. The starting dose was 0.5 mg/kg in five patients with ascites undergoing clinically indicated paracentesis (e.g. 35 mg in a 70 kg adult, administered as 35 mL of diluted food coloring solution [1 mg/mL]). If these patients demonstrated absorption of the dye (and thus gut barrier function loss), then lower doses were used in the subsequent cohorts of five patients each to establish the lowest necessary dose for detection. The medium dose was: 0.05 mg/kg—e.g. 3.5 mg in a 70 kg adult, administered as 35 mL of diluted food coloring solution (0.1 mg/mL). The low dose was: 0.005 mg/kg—e.g. 0.35 mg in a 70 kg, administered as 35 mL of diluted food coloring solution (0.01 mg/ml).

Five blood samples were drawn per subject (5 ml/draw) at 0 hour (prior to taking Blue dye #1), 1 hour, 2 hours, 4 hours, and 8 hours after administration of the dye, through clinically indicated, previously placed IV catheters. This experiment was performed on 14 subjects. In alternative embodiments, 15 ml of the abdominal fluid from the paracentesis could be saved to analyze for the presence of the dye.

B. Test in Patients with Sepsis

Test subjects with clinically determined sepsis were given enteral Blue #1 at a designated time prior to scheduled blood draw. The lowest dose necessary to detect intestinal absorption as demonstrated in section A above, was given first. If no absorption was demonstrated in section A, then 0.5 mg/kg (e.g. 35 mg in a 70 kg adult, administered as 35 ml of diluted food coloring solution [1 mg/ml]) was used. Sepsis was defined by the Surviving Sepsis Campaign [Crit Care Med. 2013; 41(2):580] (presence, probable or documented, of infection together with systemic manifestations such as fever, tachycardia, leukocytosis, hypotension, organ dysfunction, or decreased tissue perfusion). If the first five patients demonstrated absorption of the dye (and thus gut barrier function loss), then lower doses were used in the subsequent cohorts of five patients each to establish the lowest necessary dose for detection. The medium dose was: 0.05 mg/kg—e.g. 3.5 mg in a 70 kg adult, administered as 35 mL of diluted food coloring solution (0.1 mg/mL), The low dose was: 0.005 mg/kg—e.g. 0.35 mg in a 70 kg, administered as 35 ml of diluted food coloring solution (0.01 mg/ml). Five blood draws per subject (5 ml/draw): 0 hour—prior to dose, 1 hour, 2 hours, 4 hours, and 8 hours, through clinically indicated, previously placed IV catheters. 14 subjects were used in this study.

TABLE 1

| Patient Description | Clinical Status | Vasopressor support | MELD | PO | 2 H | 8 H |
| --- | --- | --- | --- | --- | --- | --- |
| Normal 1 | Normal | 0 | 6 | NPO | <0.05 | <0.05 |
| Normal 2 | Normal | 0 | 6 | NPO | <0.05 | <0.05 |
| Normal 3 | Normal | 0 | 6 | NPO | <0.05 | <0.05 |
| Normal 4 | Normal | 0 | 6 | NPO | <0.05 | <0.05 |
| Non-septic 1 | ICU | 0 | 40 | Eating | 0.5 | 0.15 |
| Non-septic 2 | ICU | 0 | 33 | Eating | <0.05 | <0.05 |
| Non-septic 3 | ICU | 0 | 17 | Eating | <0.05 | <0.05 |
| Non-septic 4 | ICU/Pressor | NE 0.4* | 36 | Eating | <0.05 | <0.05 |
| Septic 1 | ICU/Pressor | NE 0.12 | 34 | NPO x meds | 0.5 | 0.3 |
| Septic 3 | ICU/Pressor | NE 0.12 | 39 | NPO x meds | 0.7 | 0.5 |
| Septic 3 | ICU/Pressor | Vaso 4, NE 0.09, PhE 25 | 35 | NPO x meds | <0.05 | <0.05 |
| Septic 4 | ICU/Pressor | NE 0.25 | 40 | NPO x meds | 2.5 | 4.6** |
| Septic 5 | ICU/Pressor | NE 0.02 | 23 | Eating | 0.4 | 0.05 |
| Septic 6 | ICU/Pressor | Vaso 2 | 43 | NPO x meds | 1 | 1.5 |
| TTest P-value | Critical v non-critical | 0.027 | 0.0900799 | | | |
| | pressor v no pressor | 0.072 | 0.1512782 | | | |

*(<0.05 counted as 0 for stats purposes)
**Requiring pressor support to allow continuous dialysis for volume removal
* * * Died three days after measurement

Example 3: Data from Two Patients

Figure 2:
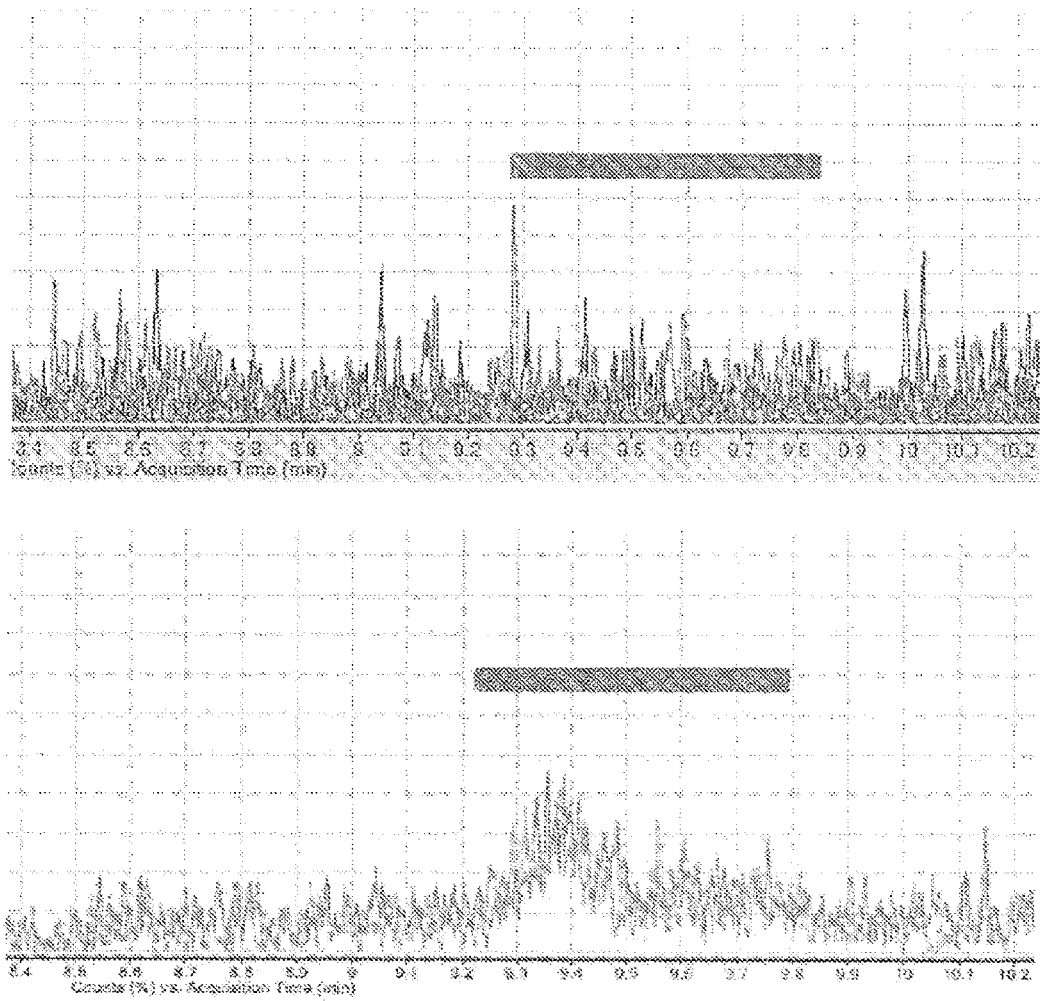
FIG. 2 depicts summary of LC/MS test results done in patients in accordance with the current invention. The upper graph depicts the tracing from a non-septic patient, in whom Blue #1 was not detectable. The lower graph shows results from a septic patient in whom Blue #1 was detectable.
Figure 3:
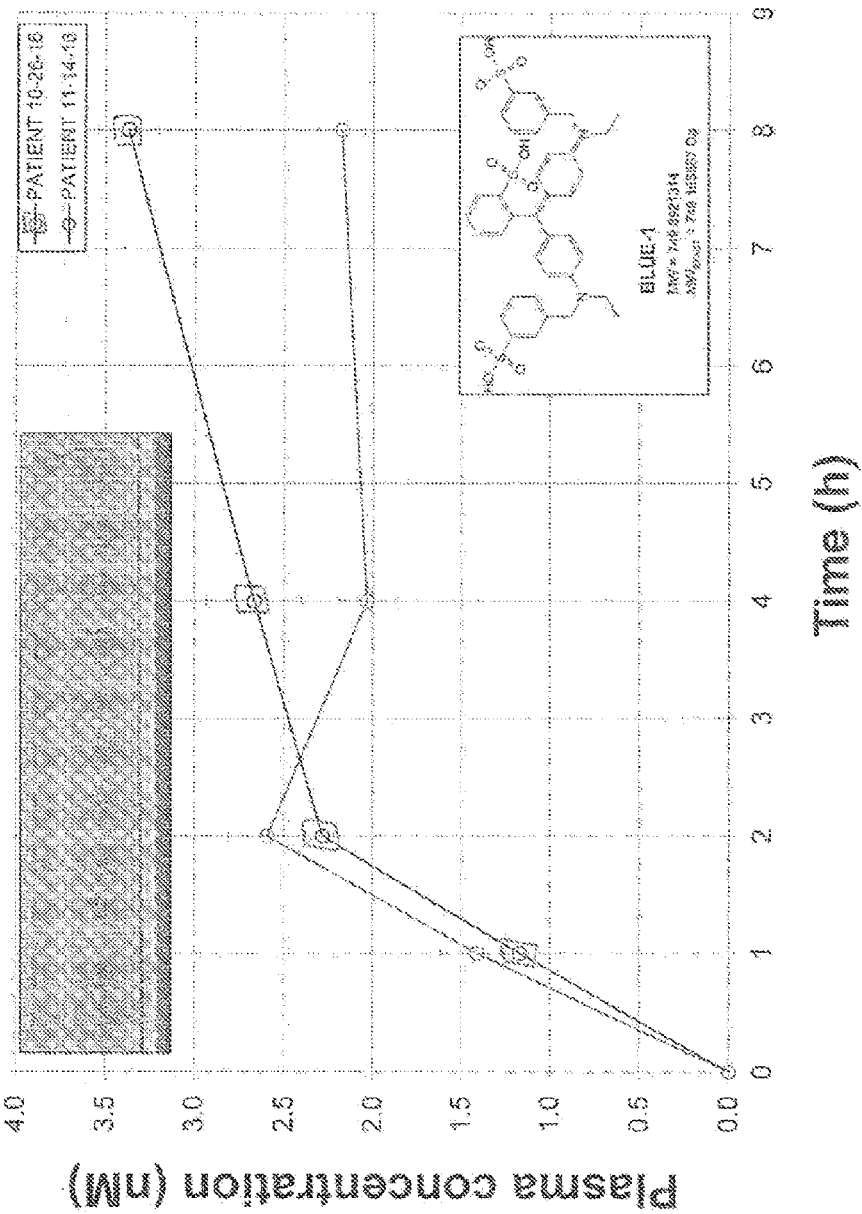
FIG. 3 is a graph showing the amount of Blue #1 permeated into the plasma of two patients at different time intervals: before ingestion of Blue #1 (zero hour), 1 hr, 2 hr, 4 hr and 8 hr after ingestion.
Figure 4:
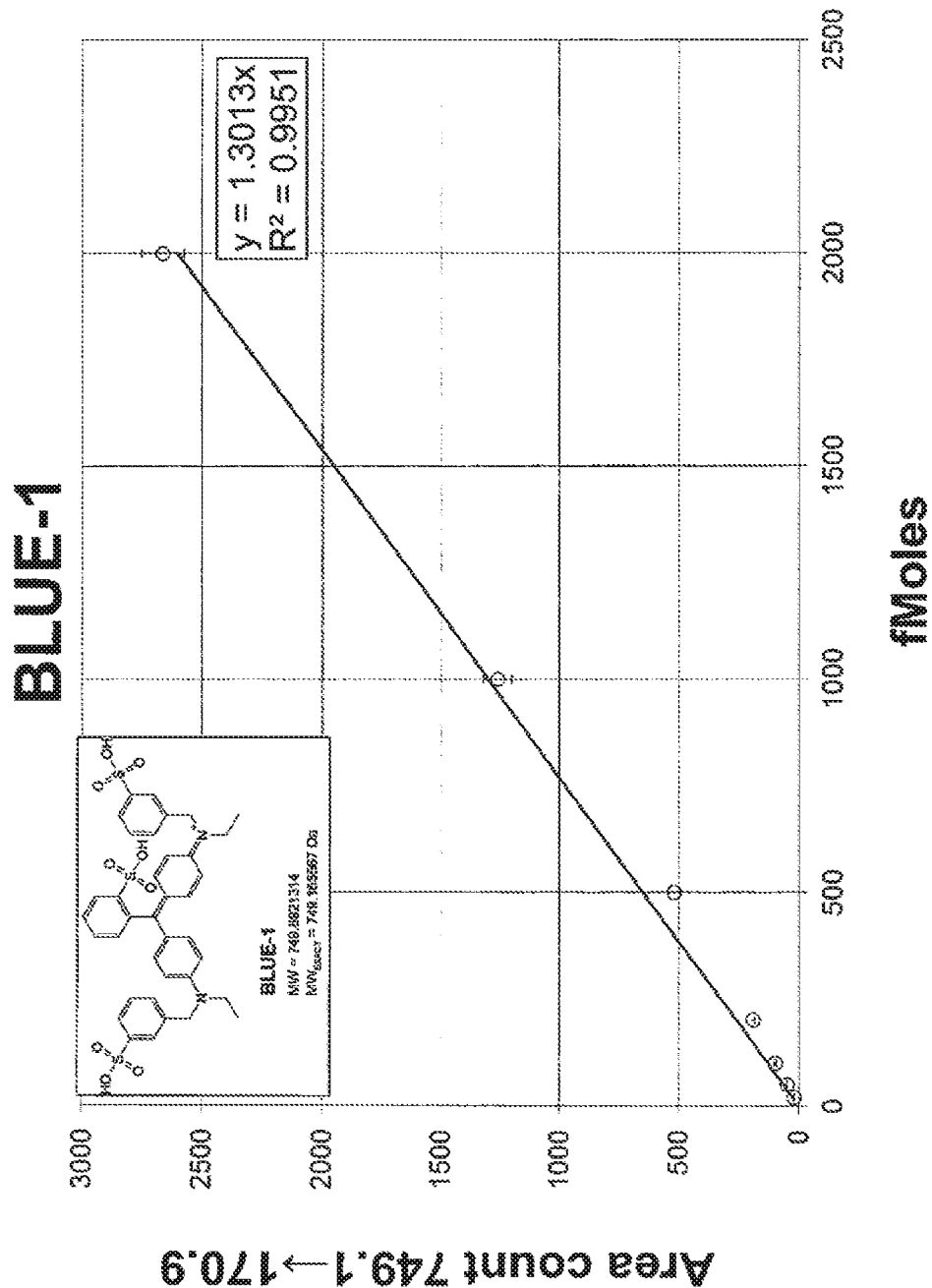
FIGS. 4-8 are examples of data charts and graphs of standard curves for various assays in accordance with the current invention.
Figure 5B:
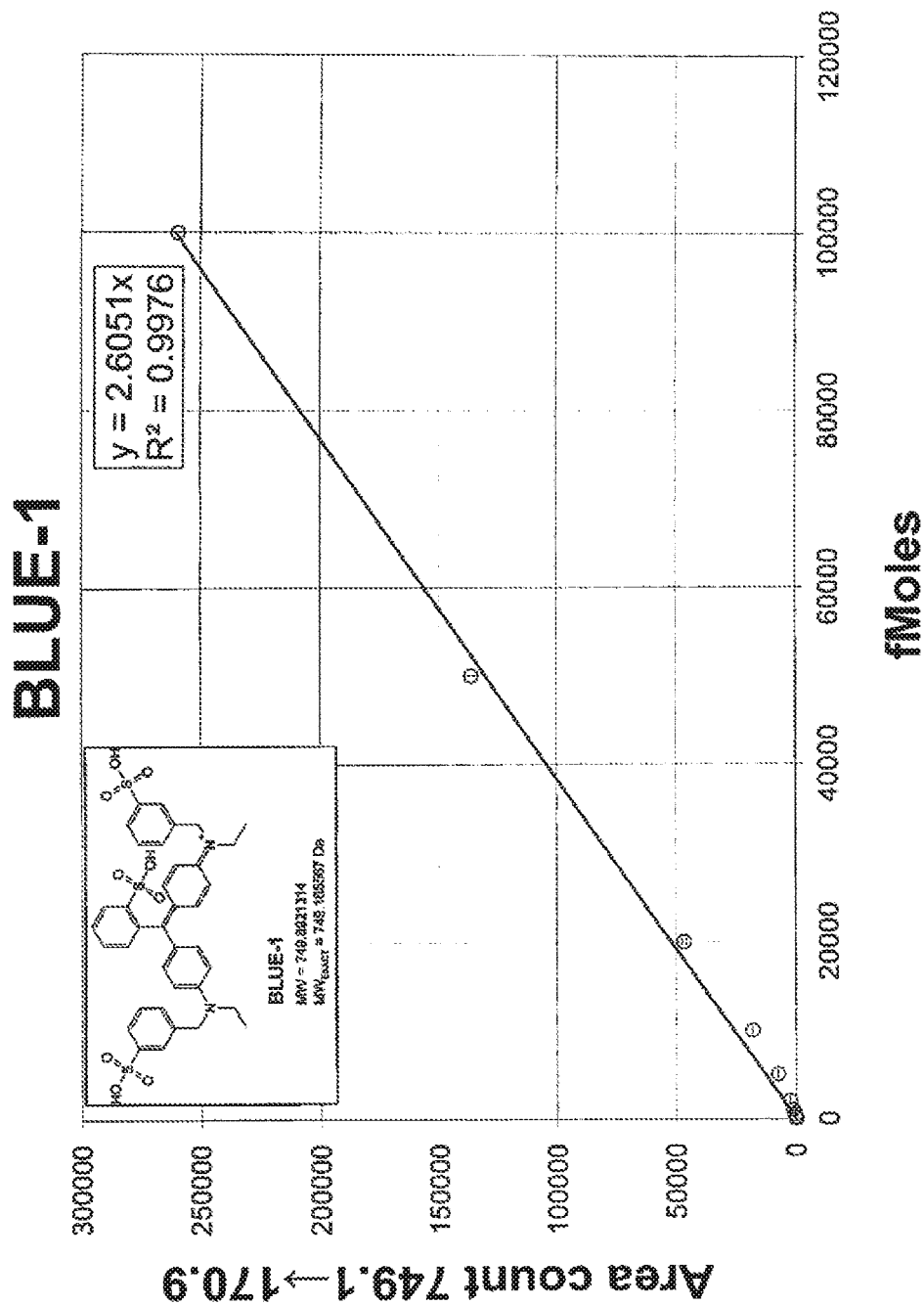
Figure 6B:
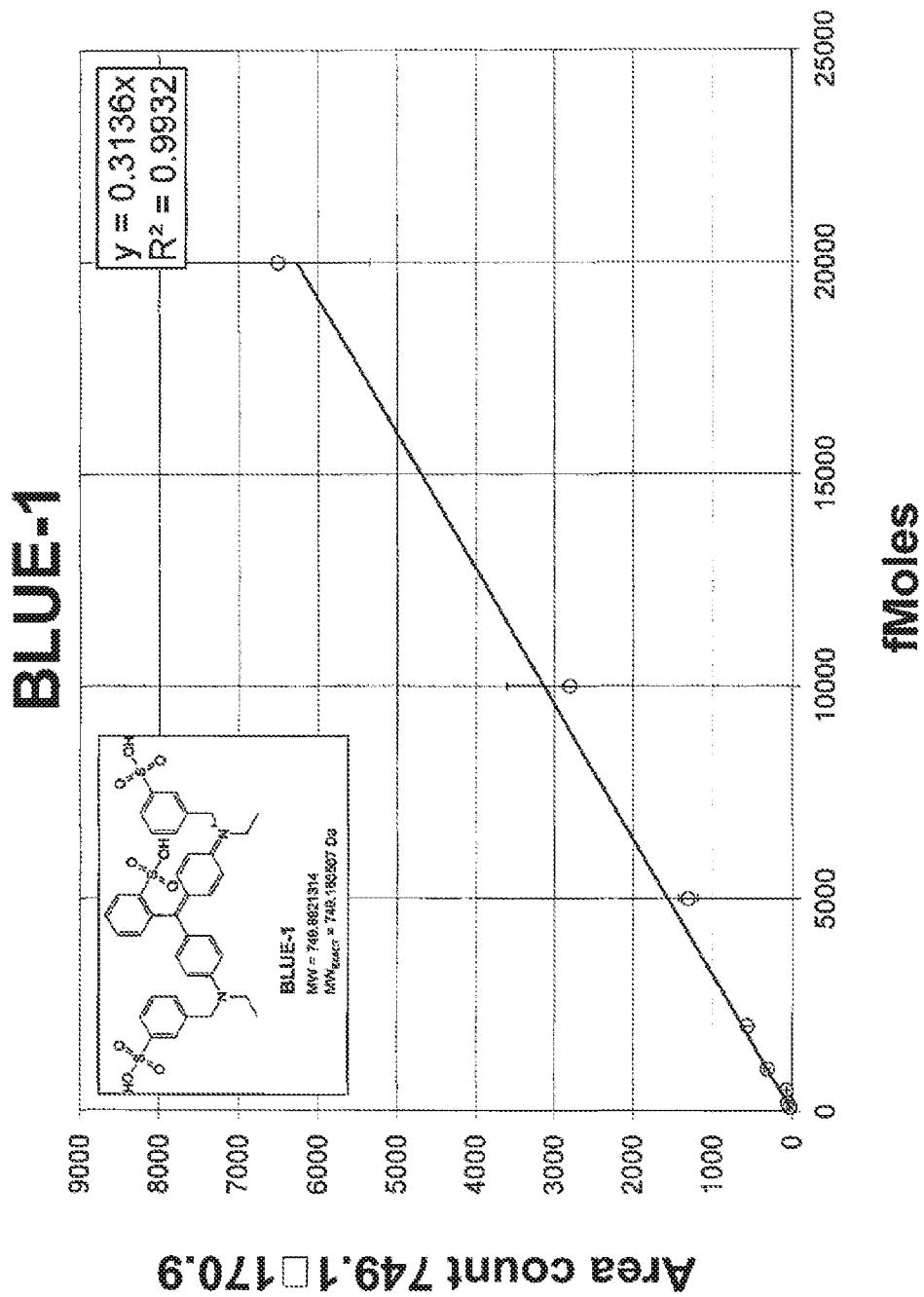
Figure 7B:
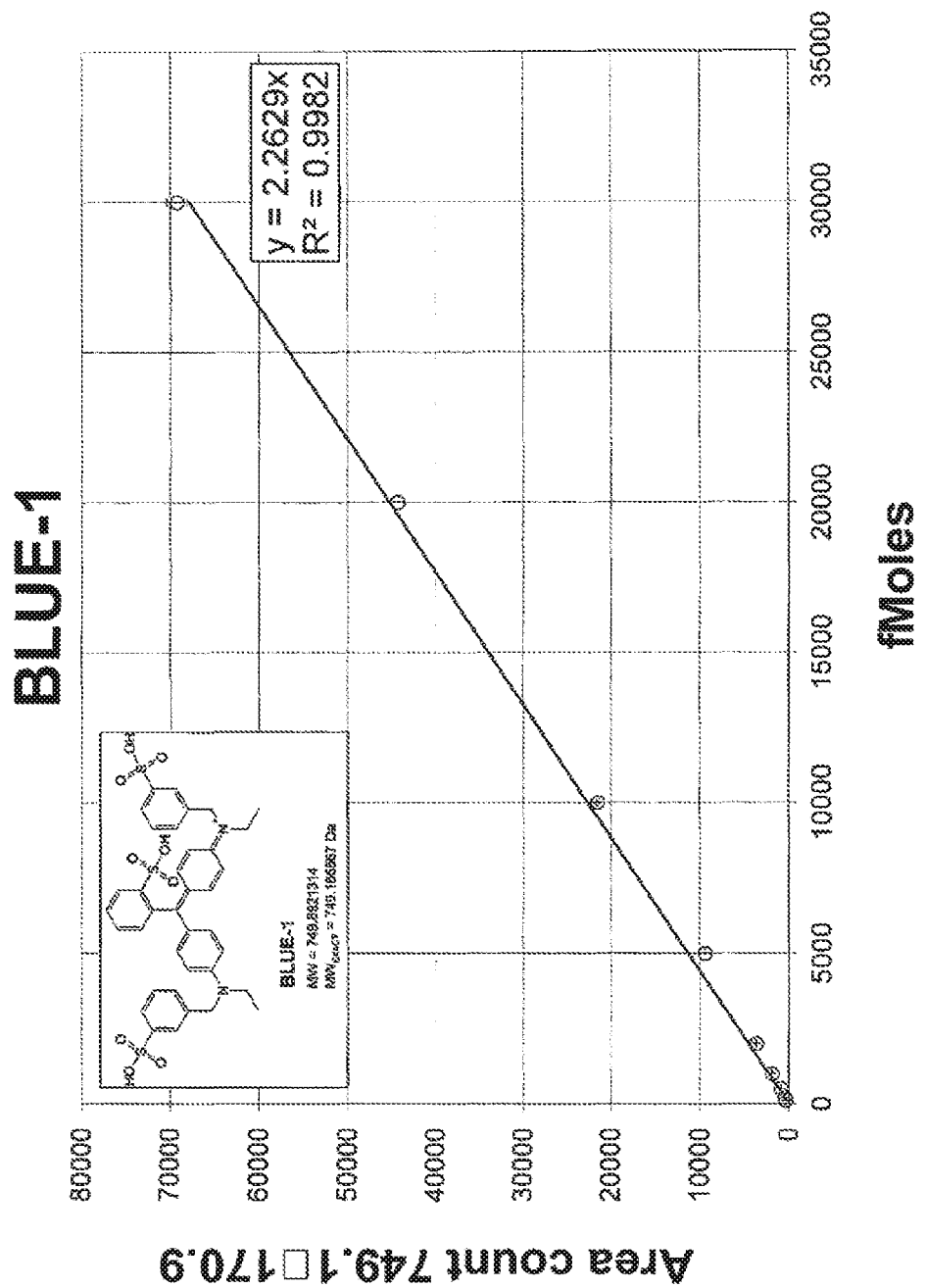
Figure 8:
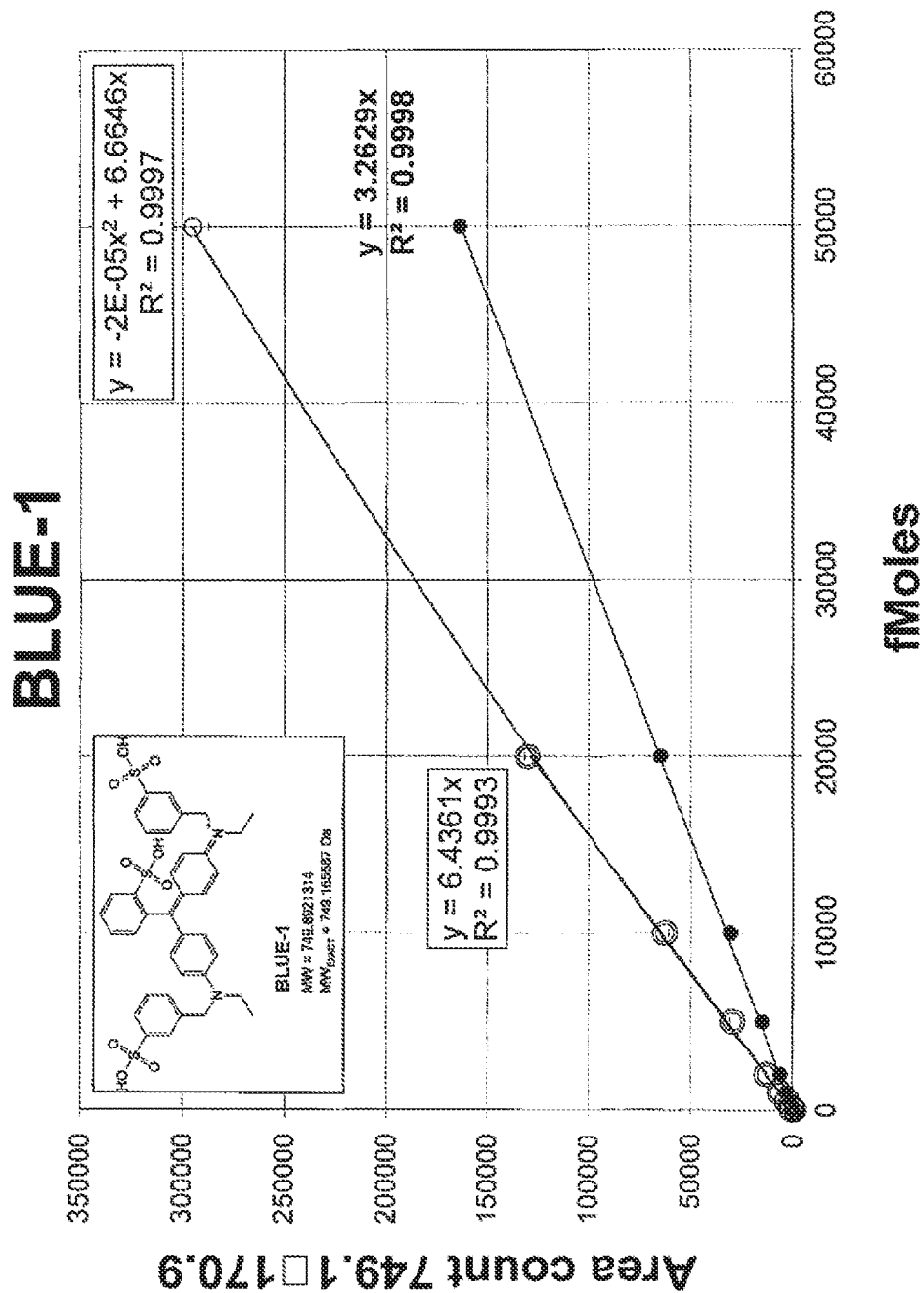

Plasma concentration of Blue-1 is shown in relation to time in two patients (10-26-16) and (11-14-16) diagnosed with sepsis. Data is shown in FIG. 2. Plasma preparation was done as shown in Example 5C below. Bzi-Arg_pNA was used as a STD. The data obtained is shown in Tables 2 and 3 below and in FIG. 3. The standard graph is FIG. 4.

TABLE 2

| (hr) | A | B | C | Standard A | Standard B | Standard C | Volume Injected (μl) | | Corrected values A | B | C | fMoles/μl (nM) A | B | C | Average | SEM |
|---|---|---|---|---|---|---|---|---|---|---|---|---|---|---|---|---|
| | | | | | | | | Plasma | | | | | | | | |
| 0 | 0 | 0 | 0 | 25098 | 23514 | 23803 | 10 | 25 | 0 | 0 | 0 | 0 | 0 | 0 | 0 | 0 |
| 1 | 63 | 37 | 41 | 23566 | 22121 | 21596 | 10 | 25 | 58.90791 | 36.85666 | 41.83401 | 1.81 | 1.13 | 1.29 | 1.41 | 0.21 |
| 2 | 69 | 93 | 84 | 21494 | 21782 | 20928 | 10 | 25 | 70.73768 | 94.08148 | 88.44444 | 2.17 | 2.89 | 2.72 | 2.59 | 0.22 |
| 4 | 80 | 59 | 68 | 23521 | 22850 | 22497 | 10 | 25 | 74.94681 | 56.8964 | 66.60445 | 2.30 | 1.75 | 2.05 | 2.03 | 0.16 |
| 8 | 81 | 66 | 66 | 22449 | 21926 | 21772 | 10 | 25 | 79.5073 | 66.32901 | 66.79817 | 2.44 | 2.04 | 2.05 | 2.18 | 0.13 |

TABLE 3

| (hr) | A | B | C | Standard A | Standard B | Standard C | Volume Injected (μl) | | Corrected values A | B | C | fMoles/μl (nM) A | B | C | Average | SEM |
|---|---|---|---|---|---|---|---|---|---|---|---|---|---|---|---|---|
| | | | | | | | | Plasma | | | | | | | | |
| 0 | 0 | 0 | 0 | 21427 | 21654 | 20808 | 10 | 25 | 0 | 0 | 0 | 0 | 0 | 0 | 0 | 0 |
| 1 | 36 | 35 | 42 | 22322 | 21832 | 21361 | 10 | 25 | 35.53762 | 35.32592 | 43.32581 | 1.09 | 1.09 | 1.33 | 1.17 | 0.08 |
| 2 | 76 | 72 | 68 | 21461 | 21371 | 21173 | 10 | 25 | 78.03377 | 74.23806 | 70.76939 | 2.40 | 2.28 | 2.18 | 2.29 | 0.06 |
| 4 | 80 | 71 | 97 | 21403 | 21004 | 20620 | 10 | 25 | 82.36341 | 74.48611 | 103.6578 | 2.53 | 2.29 | 3.19 | 2.67 | 0.27 |
| 8 | 115 | 99 | 113 | 22275 | 22045 | 21386 | 10 | 25 | 113.7625 | 98.95644 | 116.4308 | 3.50 | 3.04 | 358 | 3.37 | 0.17 |

| | |
|---|---|
| *Blue-l-A 5 uL + 995 water | |
| Blue-1-B 100 + 900 | |
| Blue-1-C 100 + 900 | |
| *Std: Bzl-Arg-pNA | Average: 22035.3 |
| 399.2->122.1 | y = 1.3013x |
| P1-E4 | 0.001 uM |
| P1-E5 | 0.01 uM |
| P1-E6 | 0.1 uM |
| P1-E7 | 1 uM |
| P1-E8 | 10 uM |

Example 4—Recovery Experiments

Recovery assays were done to optimize the extraction protocol from blood serum. Data for recovery experiments is in Table 4. Regarding the standard for the recovery experiments, standardization trials were performed to evaluate where on the HPLC column the blue dye would come and to evaluate the sensitivity of the assay. The data for standard used in the recovery experiments is shown in Table 5.

TABLE 4

| | | | | Area | | | Standard | | |
|---|---|---|---|---|---|---|---|---|---|
| First run | Glass Vial | 5 μl | STD-1 | 3266 | 3266 | 3212 | 7442 | 6810 | 6858 |
| | | 5 μl | STD-2 | 4142 | 3963 | 3792 | 8571 | 8096 | 8229 |
| | | 5 μl | STD-3 | 4392 | 4145 | 4240 | 7421 | 6824 | 7008 |
| | | 5 μl | STD-4 | 3310 | 3303 | 3319 | 5950 | 5689 | 6281 |
| | | 5 μl | STD-2 | 4566 | 4303 | 4671 | 8785 | 8922 | 9306 |
| | Glass Vial | 5 μl | SAMPLE-5 | 3200 | 3096 | 3103 | 7680 | 7311 | 7441 |
| | | 5 μl | SAMPLE-6 | 2835 | 2642 | 3444 | 7944 | 7564 | 8048 |
| | | 5 μl | SAMPLE-7 | 3934 | 3937 | 4166 | 6391 | 5836 | 5664 |
| | | 5 μl | SAMPLE-8 | 3547 | 3464 | 3742 | 8039 | 8073 | 8187 |
| | | 5 μl | SAMPLE-6 | 6429 | 3465 | 2908 | 3252 | 5604 | 6127 |

TABLE 4-continued

|  |  |  | Area |  |  | Standard |  |  |
|---|---|---|---|---|---|---|---|---|
| Glass Vial | 5 µl | STD-1 | 3527 | 2694 | 2728 | 7480 | 5929 | 6236 |
|  | 5 µl | STD-2 | 4198 | 3924 | 4184 | 7475 | 7781 | 7823 |
|  | 5 µl | STD-3 | 3633 | 4056 | 3976 | 6092 | 6765 | 6626 |
|  | 5 µl | STD-4 | 3668 | 3695 | 3464 | 5703 | 5838 | 6089 |
|  | 5 µl | STD-2 | 4191 | 4092 | 4090 | 7982 | 8453 | 8318 |
| Glass Vial | 5 µl | SAMPLE-5 | 3160 | 2969 | 3119 | 8119 | 6870 | 7033 |
|  | 5 µl | SAMPLE-6 | 10194 | 3504 | 1689 | 2014 | 5050 | 7608 |
|  | 5 µl | SAMPLE-7 | 3590 | 3752 |  | 5620 | 6115 |  |
|  | 5 µl | SAMPLE-8 | 3558 | 3117 | 3427 | 7596 | 7474 | 8166 |
|  | 5 µl | SAMPLE-6 | 4904 | 2404 | 3048 | 3308 | 4786 | 4710 |

TABLE 5

Figure 9:
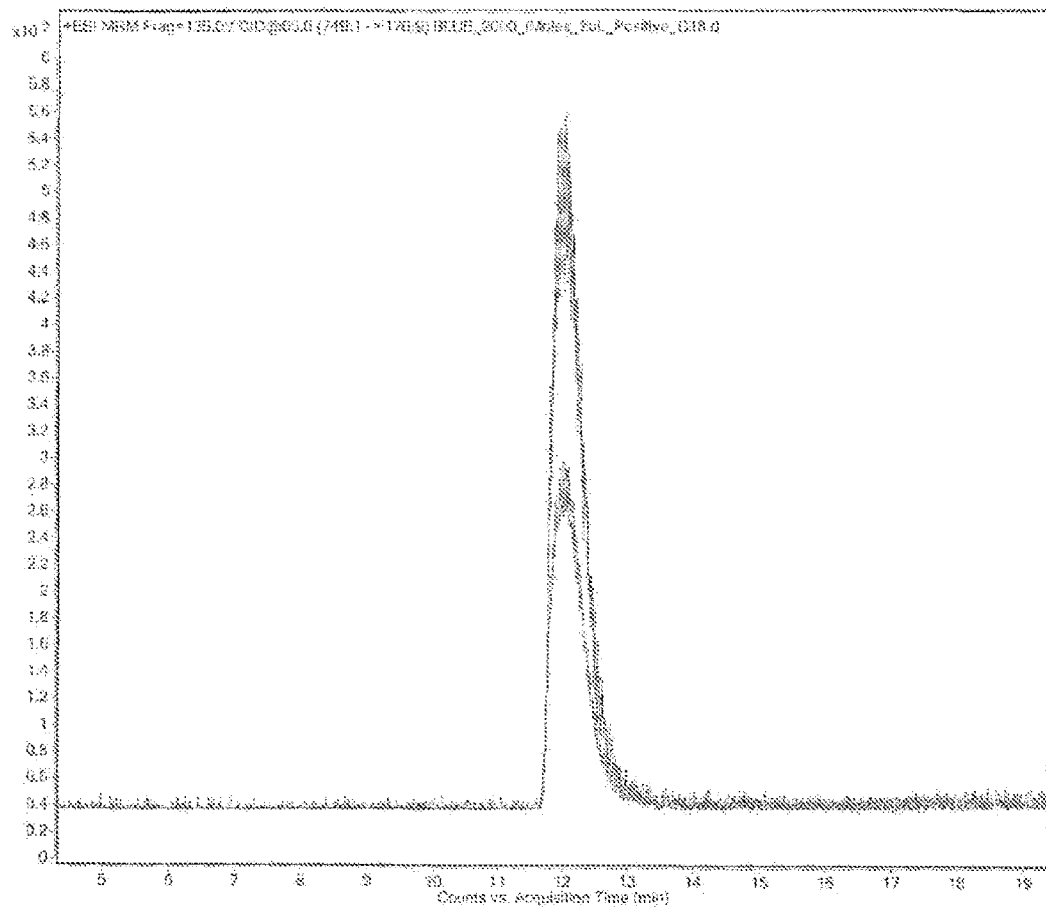
FIG. 9 depicts a comparison of counts versus acquisition time for an LC/MS assay with or without electrospray ionization.

| fMoles injected |  |  |  | Average | sem |
|---|---|---|---|---|---|
| 50000 | 167893.0 | 159423.0 | 164240.0 | 163852.0 | 2452.763 |
| 20000 | 65291.0 | 64778.0 | 64258.0 | 64775.7 | 298.2037 |
| 10000 | 31031.0 | 29302.0 | 31790.0 | 30707.7 | 736.1939 |
| 5000 | 14900.0 | 15501.0 | 15250.0 | 15217.0 | 174.2766 |
| 2000 | 6124.0 | 6307.0 | 5988.0 | 6139.7 | 92.41994 |
| 1000 | 2996.0 | 3067.0 | 3127.0 | 3063.3 | 37.86086 |
| 500 | 1259.0 | 1327.0 | 1360.0 | 1315.3 | 29.73401 |
| 200 | 555.0 | 590.0 | 573.0 | 572.7 | 10.105 |
| 100 | 291.0 | 327.0 | 293.0 | 303.7 | 11.68094 |
| 50 | 122.0 | 158.0 | 145.0 | 141.7 | 10.5251 |
| 20 | 82.0 | 95.0 | 84.0 | 87.0 | 4.041452 |
| 10 |  |  |  |  |  | from 100% A:0% B to 0% A:100% B was used to separate the various molecules from the extraction. Parameters and data are presented in Tables 6 and 7. The data is shown in FIG. 9.

TABLE 6

| ESI− | ESI+ |
|---|---|
| 747.1-> 170.1 | 749.1->170.9 |
| CAV3 | CAV7 |
| Fragm 125 | Fragm 135 |
| Coil Energy 75 | Coil Energy 55 or 65 |
|  | (higher response) |

TABLE 7

| Tube |  |  |  |  |  |  |  |  |  | Blue1 |  |
|---|---|---|---|---|---|---|---|---|---|---|---|
| Concentration |  | Injection |  |  |  | ESI+ |  |  |  |  |  |
| (µM) | (M) | Vol. (µl) | Mol | pMol | Fmol |  | Area Std Curve |  |  | Average | SEM |
| 10.00 | 1.0E−05 | 5 | 5.0E−11 | 50 | 50000 | 279447 | 286896 | 297287 | 316181 | 294952.8 | 7965.7 |
| 5.00 | 5.0E−06 | 4 | 2.0E−11 | 20 | 20000 | 128646 | 130021 | 132083 | 135881 | 130250.0 | 1575.0 |
| 5.00 | 5.0E−06 | 2 | 1.0E−11 | 10 | 10000 | 56217 | 64954 | 65248 | 63885 | 62576.0 | 2139.8 |
| 1.00 | 1.0E−06 | 5 | 5.0E−12 | 5 | 5000 | 28315 | 28336 | 30126 | 31595 | 29593.0 | 790.9 |
| 1.00 | 1.0E−06 | 2 | 2.0E−12 | 2 | 2000 | 12686 | 13018 | 13037 | 13224 | 12991.3 | 111.9 |
| 1.00 | 1.0E−06 | 1 | 1.0E−12 | 1 | 1000 | 6482 | 6665 | 6395 | 6825 | 6591.8 | 96.0 |
| 0.10 | 1.0E−07 | 5 | 5.0E−13 | 0.5 | 500 | 2769 | 2875 | 2926 | 3024 | 2898.5 | 53.1 |
| 0.10 | 1.0E−07 | 2 | 2.0E−13 | 0.2 | 200 | 1298 | 1301 | 1249 | 1351 | 1299.8 | 20.8 |
| 0.10 | 1.0E−07 | 1 | 1.0E−13 | 0.1 | 100 | 676 | 674 | 675 | 653 | 669.5 | 5.5 |
| 0.010 | 1.0E−08 | 5 | 5.0E−14 | 0.05 | 50 | 290 | 292 | 300 | 229 | 277.8 | 16.4 |
| 0.010 | 1.0E−08 | 2 | 2.0E−14 | 0.02 | 20 | 150 | 151 | 137 | 158 | 149.0 | 4.4 |
| 0.010 | 1.0E−08 | 1 | 1.0E−14 | 0.01 | 10 | 87 | 82 | 79 | 76 | 81.0 | 2.3 |
| 0.001 | 1.0E−09 | 5 | 5.0E−15 | 0.005 | 5 |  | 47 | 59 | 37 | 47.7 | 5.5 |
| 0.001 | 1.0E−09 | 2 | 2.0E−15 | 0.002 | 2 |  |  |  |  |  |  |
| 0.001 | 1.0E−09 | 1 | 1.0E−15 | 0.001 | 1 |  |  |  |  |  |  |

TABLE 5-continued

| fMoles injected |  |  |  | Average | sem |
|---|---|---|---|---|---|
| 5 |  |  |  |  |  |
| 2 |  |  |  |  |  |
| 1 |  |  |  |  |  |

Example 5

The assay was performed with and without electrospray ionization, Zorbax SB-C18 1.8 µm 2.1×50 mm column was used. The HPLC buffers used were: Buffer A=20 mM HCOONH4, 0.1% FA, water and buffer B=ACN: MeOH=>7:3 (vol:vol) (0-3 min 100% A, 3-15 min=>0-100% B, 100 µL/min). To run the HPLC, a gradient going Example 6. Methodology A. Cohorts of Subjects 34 subjects are divided into 3 groups:

Group 1 included normal subjects (4 for example) with a healthy state.

Group 2 was optional. It can include patients that have ascites and are undergoing a clinically indicated paracentesis or removal of fluid from the abdomen. 14 or more patients will be used for this group.

Group 3 included patients having signs and symptoms of sepsis or low blood pressure caused by infection or inflammation. 14 or more patients are used for this group.

B. Collection of Samples

Subjects were asked to drink a blue food coloring solution, (GATORADE for example) at 0.5 mg/kg (35 ml for a 70 kg human subject). Then a blood sample was drawn (e.g. 5 ml) at five different time periods for each subject: immediately before the drink (time zero), 1 hour, 2 hour, 4 hour and 8 hours after the drink. Subjects in Group 2 also had some of their abdominal fluid from the paracentesis saved to analyze for the presence of the dye, Plasma was prepared according to the method in the following example.

C. Plasma Preparation

Blood samples drawn from subjects in the groups above were prepared as follows:

1) one volume of plasma was mixed with 3 volumes of (1:3→IPA:CAN+0.1% TFA);

2) after spin-down, 1800 µl of supernatant was evaporated (for example, by a Speed-Vac)

3) residue was re-suspended in 180 µl of 50% NMP in water (BLUE-I is soluble in both)

4) 10 µl of the re-suspended residue was injected onto a mass spectrophotometer for each analysis which corresponds to 25 µl of "pure plasma". Quantitative analysis of the peak corresponding to the mass of Blue #1 was performed to see how much of the dye had been absorbed. Bzl-Arg_pNA is an example of a standard that worked with this assay.

D. Statistics and Data Analysis a) Population for Analysis: All patients entering the study were included in the final analysis. Data on patients were summarized and compared among the groups.

b) Demographics and Baseline Characteristics: Demographic and baseline characteristics of the subjects were summarized descriptively by means and standard deviations for continuous variables, and frequency distribution for categorical variables. Summaries were performed based on all subjects.

c) Correlation Analyses: Clinical variables and outcomes were used to correlate with the amount of absorbed food coloring. These were calculated and summarized.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for evaluating the integrity of an intestinal barrier in a mammalian subject comprising:
    a) administering to the mammalian subject a pharmaceutical composition comprising from 0.1 mg/kg to 1 mg/kg of disodium; 2-[[4-[ethyl-[(3-sulfonatophenyl)methyl]amino]phenyl]-[4-[ethyl-[(3-sulfonatophenyl)methyl]azaniumylidene]cyclohexa-2,5-dien-1-ylidene]methyl]benzenesulfonate ("Blue #1");
    b) assaying or measuring Blue #1 in a blood sample collected from the mammalian subject within 24 hours after the mammalian subject has been administered the pharmaceutical composition; and
    c) evaluating the integrity of the intestinal barrier of the mammalian subject based on the amount of Blue #1 measured in the blood sample;
    wherein the pharmaceutical composition is administered to the mammalian subject orally or nasogastrically;
    wherein the pharmaceutical composition further comprises a positive control dye; and
    wherein the positive control dye is 3,3'-dioxo-2,2'-bisindolyden-5,5'-disulfonic acid disodium salt.

2. The method of claim 1, wherein the pharmaceutical composition is a liquid composition.

3. The method of claim 2, wherein the volume of the pharmaceutical composition is between 1 ml and 500 ml.

4. The method of claim 1, wherein the pharmaceutical composition includes 0.5 mg/kg of Blue #1.

5. The method of claim 1, wherein measuring Blue #1 is done using mass spectrometry, HPLC, light spectroscopy, or any combination thereof.

6. The method of claim 1, wherein the blood sample is collected from the subject 1 to 8 hours after the mammalian subject has been administered the pharmaceutical composition comprising Blue #1.

7. The method of claim 1, wherein the assaying is done from multiple samples collected from the mammalian subject at different intervals after the subject has been administered the pharmaceutical composition comprising Blue #1.

8. The method of claim 1, wherein the blood sample is a plasma or serum sample.

9. The method of claim 1, wherein the mammalian subject has symptoms or is at risk for ascites, sepsis, intestinal hypoperfusion, celiac disease, or inflammatory bowel disease.

10. The method of claim 1, wherein the mammalian subject has experienced trauma or major surgery within 72 hours prior to step a).

11. The method of claim 1, wherein the mammalian subject has been diagnosed with sepsis, intestinal hypoperfusion, celiac disease, trauma, organ failure, or inflammatory bowel disease.

12. The method of claim 1, wherein the mammalian subject has not ingested any liquid or food within 8 hours prior to step a).

13. The method of claim 1, wherein when Blue #1 is measured to be at least 1 femtomole per 5 ml in the blood sample, the method further comprises treating the mammalian subject for intestinal barrier dysfunction.

14. The method of claim 13, wherein treating the mammalian subject comprises control feeding, administration of intestinal antibiotics, administration of intravascular antibiotics, or any combination thereof.

* * * * *